(12) United States Patent
Berler (10) Patent No.: US 11,497,860 B2
(45) Date of Patent: Nov. 15, 2022

(54) ULTRA-LOW WASTE DISPOSABLE SAFETY SYRINGE FOR LOW DOSE INJECTIONS

(71) Applicant: Sharps Technology, Inc., Melville, NY (US)

(72) Inventor: Barry B. Berler, Huntingdon Valley, PA (US)

(73) Assignee: Sharps Technology, Inc., Melville, NY (US)

( * ) Notice: Subject to any disclaimer, the term of this patent is extended or adjusted under 35 U.S.C. 154(b) by 114 days.

(21) Appl. No.: 16/908,608

(22) Filed: Jun. 22, 2020

(65) Prior Publication Data

US 2020/0405975 A1    Dec. 31, 2020

Related U.S. Application Data

(60) Provisional application No. 62/867,815, filed on Jun. 27, 2019.

(51) Int. Cl.
*A61M 5/32* (2006.01)
*A61M 5/50* (2006.01)
*A61M 5/31* (2006.01)

(52) U.S. Cl.
CPC .......... *A61M 5/326* (2013.01); *A61M 5/3129* (2013.01); *A61M 5/5086* (2013.01); *A61M 2005/3265* (2013.01); *A61M 2205/584* (2013.01)

(58) Field of Classification Search
CPC ............................................. A61M 2005/3265
See application file for complete search history.

(56) References Cited

U.S. PATENT DOCUMENTS

| | | |
|---|---|---|
| 4,559,043 A | 12/1985 | Whitehouse et al. |
| 4,986,813 A | 1/1991 | Blake, III et al. |
| 5,104,384 A | 4/1992 | Parry |
| 5,205,826 A | 4/1993 | Chen |
| 5,306,258 A | 4/1994 | de la Fuente |
| 5,314,503 A | 5/1994 | Bobrove et al. |
| 5,370,628 A | 12/1994 | Allison et al. |

(Continued)

FOREIGN PATENT DOCUMENTS

| | | |
|---|---|---|
| CA | 2236049 | 7/2006 |
| EP | 1 645 302 | 2/2007 |

(Continued)

*Primary Examiner* — Emily L Schmidt
(74) *Attorney, Agent, or Firm* — LaMorte & Associates, P.C.

(57) ABSTRACT

A needle and syringe system, wherein a needle head is attached to a syringe assembly. The syringe assembly includes a syringe barrel and a plunger rod with a plunger head. A needle base is affixed to the syringe barrel. A tubular cavity is formed in the needle base and a post extends through the tubular cavity. A needle extends through the post. A spacer is provided. The spacer is displaced into the tubular cavity within the needle base as the plunger head is advanced within the syringe barrel. A protective cover is disposed about the needle base. The spacer moves the protective cover between a first position and a second position as the spacer is displaced into the tubular cavity. As the protective cover moves between positions, the protective cover surrounds the needle and prevents the needle from causing any inadvertent needle stick injuries.

14 Claims, 5 Drawing Sheets

(56) References Cited

U.S. PATENT DOCUMENTS

| | | | |
|---|---|---|---|
| 5,385,555 | A | 1/1995 | Hausser |
| 5,460,611 | A | 10/1995 | Alexander |
| 5,733,264 | A | 3/1998 | Flowers |
| 5,891,092 | A * | 4/1999 | Castellano .......... A61M 5/3257 604/110 |
| 5,902,270 | A | 5/1999 | Jentzen |
| 6,616,636 | B2 | 9/2003 | Lee |
| 6,626,863 | B1 | 9/2003 | Berler |
| 2007/0016140 | A1 | 1/2007 | Berler |
| 2007/0016145 | A1 | 1/2007 | Berler |
| 2008/0009808 | A1 | 1/2008 | Berler |
| 2008/0097337 | A1 | 4/2008 | Judd et al. |
| 2008/0319346 | A1 | 12/2008 | Crawford et al. |
| 2016/0279333 | A1 | 9/2016 | Russo et al. |
| 2016/0279344 | A1 | 9/2016 | Shluzas et al. |
| 2016/0367764 | A1 | 12/2016 | Doyle |
| 2017/0319791 | A1 | 11/2017 | Giambattista et al. |

FOREIGN PATENT DOCUMENTS

| | | |
|---|---|---|
| WO | WO 91/12841 | 9/1991 |
| WO | WO 2004/035120 | 4/2004 |

\* cited by examiner

ULTRA-LOW WASTE DISPOSABLE SAFETY SYRINGE FOR LOW DOSE INJECTIONS

RELATED APPLICATIONS

This application claims the benefit of U.S. Provisional Patent Application No. 62/867,815 filed Jun. 27, 2019.

BACKGROUND OF THE INVENTION

1. Field of the Invention

In general, the present invention relates to syringes that are used to make injections through a needle or cannula. More particularly, the present invention relates to safety syringes that are designed to shield the needle after use and to minimize the amount of injection material retained within the syringe after the syringe is used.

2. Prior Art Description

Healthcare professionals perform millions of injections each year. The injections are typically performed using a hypodermic needle and a syringe. The length of the hypodermic needle and the gauge of the needle depend upon the application and whether the injection is intramuscular, subcutaneous, intravenous, or intradermal. The compounds being injected also vary widely. Some injection materials, such as saline, are very inexpensive. However, many pharmaceutical compounds, such as certain gene therapy compounds, can cost tens of thousands of dollars per injection. As such, a fraction of a milliliter of the pharmaceutical can be worth hundreds of dollars.

When a traditional hypodermic needle and syringe are used to perform an injection, there is inevitably some volume of injection material that remains within the needle and syringe after the injection is complete. The pharmaceutical material remaining is thrown away with the needle and syringe after the injection. This wasted pharmaceutical material adds up to billions of dollars in wasted pharmaceuticals, when all injections are considered.

In the prior art, thought is rarely given to the volume of residual material that inherently remains within a hypodermic syringe and needle. Some needle and syringe assemblies have been designed where a syringe plunger and a needle head make flush contact. Such prior art designs are exemplified by U.S. Pat. No. 6,616,636 to Lee and U.S. Pat. No. 5,902,270 to Jentzen. However, in a real healthcare environment, such as a hospital, different syringes are used with many different needle heads, depending upon the specific medical application. Some needle head and syringe combinations are efficient in the discharge of pharmaceutical compounds and some are not.

The problem becomes more complicated when a needle head and syringe are part of a safety syringe assembly. Safety syringe assemblies are designed to both perform an injection and to provide some mechanism for minimizing the likelihood of a needle stick injury. Needle stick injuries are commonplace among healthcare workers. Needle stick injuries are defined by the United States National Institute of Occupational Safety and Health as injuries caused by needles such as hypodermic needles, blood collection needles, intravenous (IV) stylets, and needles used to connect parts of IV delivery systems. Needle stick injuries can transfer blood-borne pathogens such as Hepatitis B virus, Hepatitis C virus, Human Immunodeficiency Virus (HIV) and Covid-19. For healthcare workers, needle stick injuries are responsible for a significant proportion of these diseases in the healthcare workforce.

It has been estimated by the Centers for Disease Control, that in the United States of America, that more than three million healthcare workers are exposed to blood and bodily fluids via needle mishaps each year. Most healthcare workers are trained in procedures for using and disposing of used needles. For example, needles should not be recapped, in order to prevent the potential for needle stick injuries. However, many studies have revealed that recapping is still prevalent among healthcare workers.

In an attempt to reduce the number of needle stick injuries, various safety needles have been developed that act to automatically cover a needle the instant the needle is retracted from the skin. This is typically accomplished by advancing a tubular sheath along the shaft of the needle until the sheath covers the tip of the needle. Such prior art is exemplified by U.S. Pat. No. 6,626,863, U.S. Patent Application Publication No. 2007/0016140, U.S. Patent Application Publication No. 2007/0016145, and U.S. Patent Application Publication No. 2008/009808. However, integrating a safety mechanism within a needle head typically takes additional room within the needle head. More room in the needle head means that there is more dead space in the needle head where residual pharmaceutical compounds can collect. As a consequence, there are often opposing concerns that must be balanced in a design. The safety features of a design are balanced with the wasted pharmaceutical retained because of the safety features.

A need therefore exists for an improved hypodermic needle and syringe assembly where the needle is automatically shielded after an injection and wherein the assembly does not retain any significant volume of the material being injected. This need is met by the present invention as described and claimed below.

SUMMARY OF THE INVENTION

The present invention is a needle and syringe system, wherein a needle head is attached to a syringe assembly. The syringe assembly includes a syringe barrel. A plunger rod is provided with a plunger head that can reciprocally move within the syringe barrel.

A needle base is affixed to the syringe barrel. The needle base has a first end and a second end at opposite points along a central axis. A tubular cavity is formed in the needle base and a post extends through the tubular cavity. The tubular cavity is accessible from the first end of the needle base.

A needle extends into the needle base along the central axis. The needle extends through the post and is open at the first end of the needle base to receive the contents of the syringe barrel. A spacer is provided. The spacer is displaced into the tubular cavity within the needle base as the plunger head is advanced within the syringe barrel.

A protective cover is disposed about the needle base. The spacer moves the protective cover between a first position and a second position as the spacer is displaced into the tubular cavity. As the protective cover moves between positions, the protective cover surrounds the needle and prevents the needle from causing any inadvertent needle stick injuries.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

The present invention needle and syringe system can be configured in many ways and can be adapted for use in many applications. However, only one exemplary embodiment is selected for the purposes of description and illustration. The illustrated embodiment, however, is merely exemplary and should not be considered a limitation when interpreting the scope of the appended claims.

Figure 1:
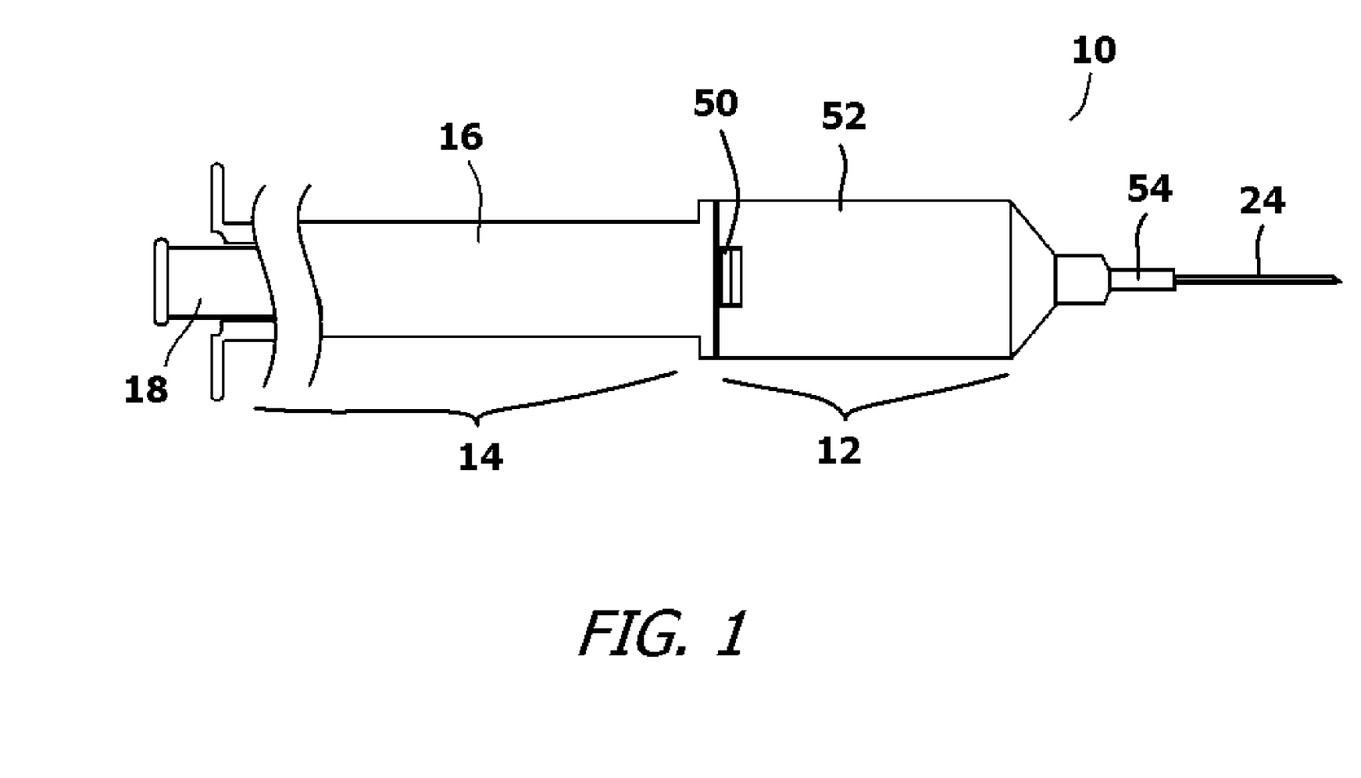
FIG. 1 shows the head of an exemplary needle and syringe system in a condition ready for use with its needle exposed.
Figure 2:
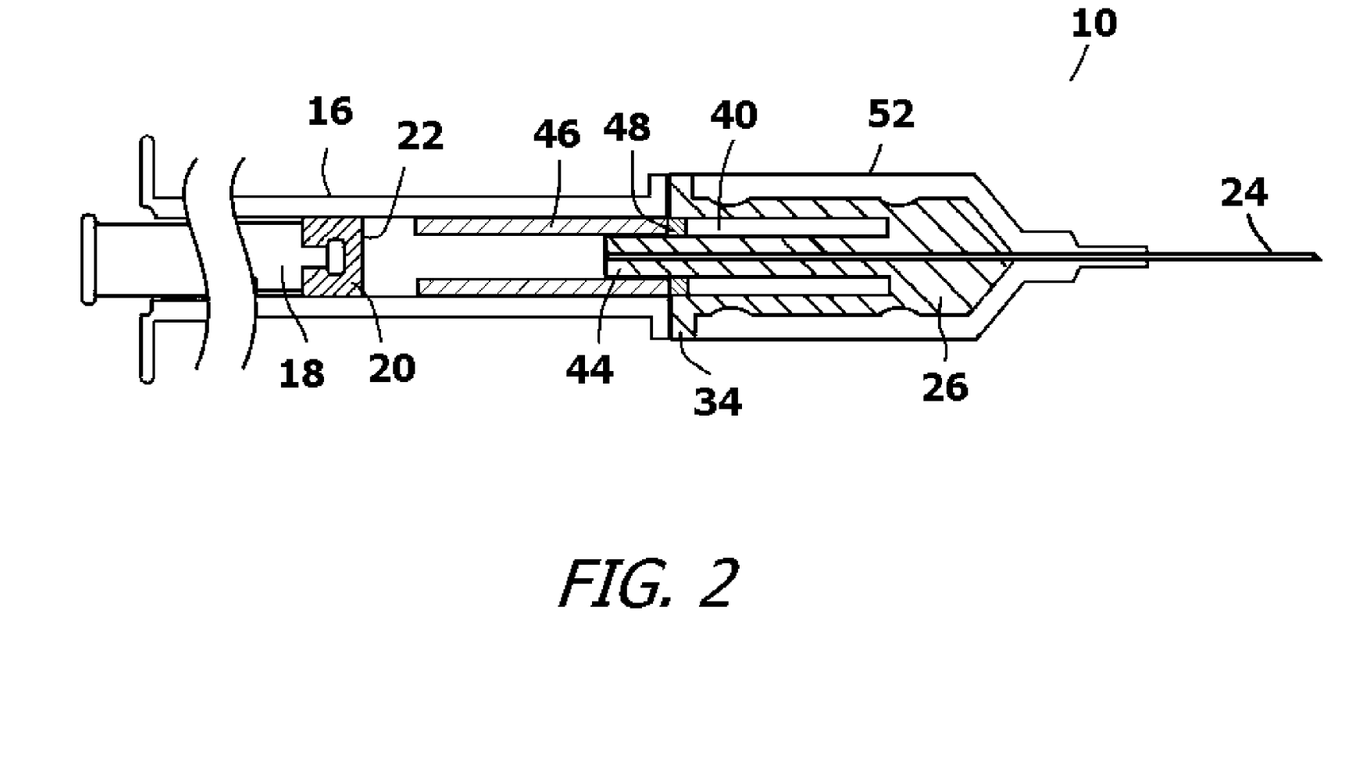
FIG. 2 is a cross-sectional view of the embodiment of FIG. 1.
Figure 3:
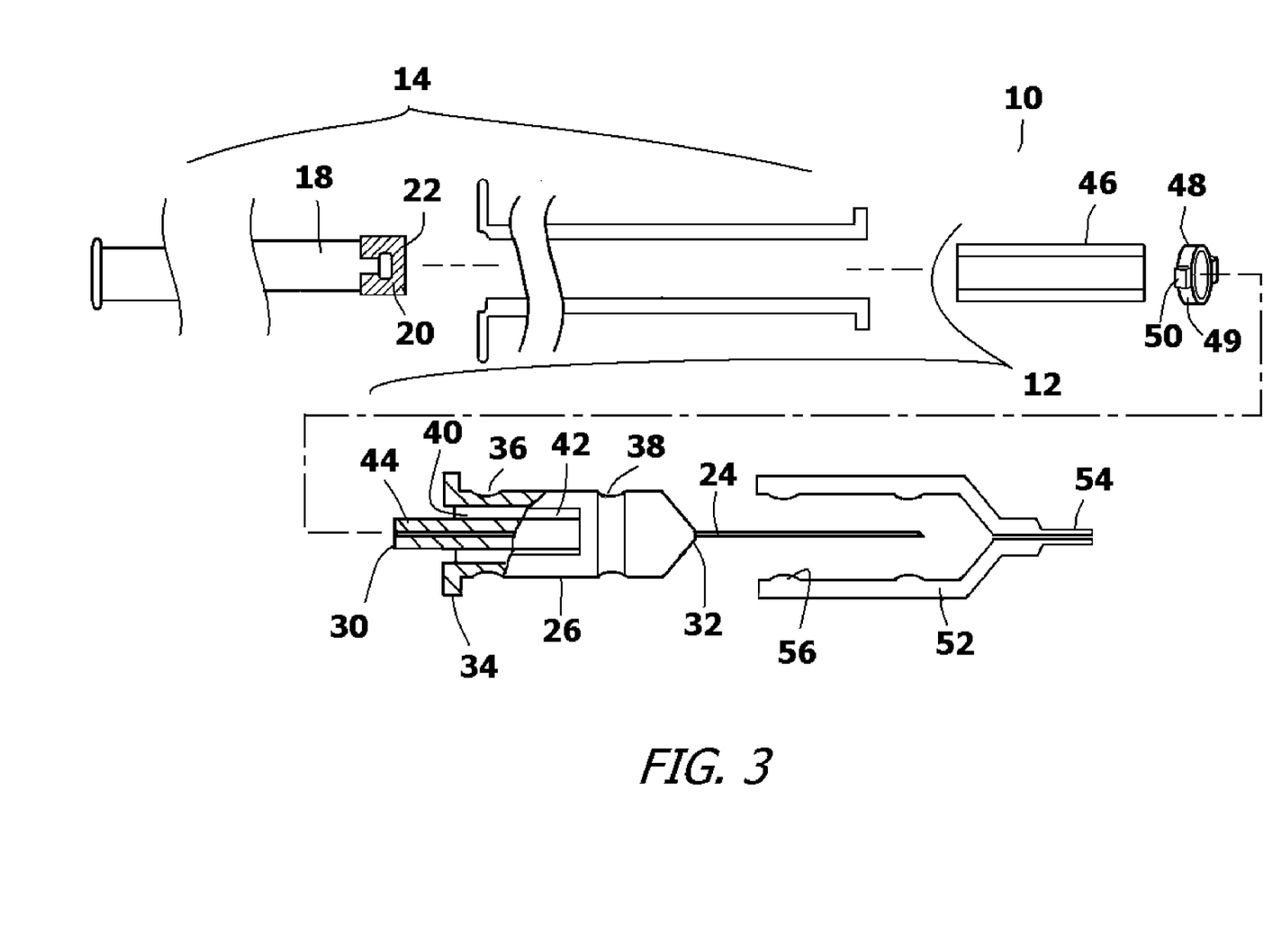
FIG. 3 shows an exploded view of the exemplary embodiment.

Referring to FIG. 1, FIG. 2, and FIG. 3, the present invention needle and syringe system 10 is shown. In the shown embodiment, the needle and syringe system 10 includes two primary subassemblies that are selectively joined. The primary subassemblies include a head subassembly 12 and a syringe subassembly 14. The head subassembly 12 mechanically engages the syringe subassembly 14 with a mechanical connection, or can be bonded to the syringe subassembly 14 using adhesive or a plastic weld. Regardless, the connection between the syringe subassembly 14 and the head subassembly 12 is fluid impervious.

The syringe subassembly 14 includes a syringe barrel 16 and a plunger rod 18 that extends into the syringe barrel 16. The plunger rod 18 can be manually advanced through the syringe barrel 16 toward the head subassembly 12. The plunger rod 18 terminates with an elastomeric piston head 20. The elastomeric piston head 20 seals against the interior of the syringe barrel 16 as the plunger rod 18 moves within the syringe barrel 16. The piston head 20 has a flat front surface 22 that faces the piston head 20 in the syringe barrel 16.

The head subassembly 12 holds a needle 24. The needle 24 is supported in the head subassembly 12 by a plastic needle base 26. The needle base 26 has a complex shape. The needle base 26 is symmetrically formed around a central axis 28, wherein the needle 24 is aligned with the central axis 28. Along the central axis 28, the needle base 26 has a first end 30 and an opposite second end 32. The first end 30 of the needle base 26 extends into the syringe barrel 16 and faces the piston head 20.

A flange 34 is formed near the first end 30 on the exterior of the needle base 26. The flange 34 is either mechanically connected, or adhered to, the syringe barrel 16. This joins the needle base 26 to the syringe barrel 16. Two locking depressions 36, 38 are formed on the exterior of the needle base 26. The first locking depression 36 is positioned near the first end 30 of the needle base 26 and the second locking depression 38 is positioned near the second end 32 of the needle base 26.

A tubular cavity 40 is formed in the first end 30 of the needle base 26. The tubular cavity 40 is accessible through two side slots 42 that are formed in opposite sides of the needle base 26. The slots 42 extend from the flange 34 to the distal end of the tubular cavity 40. The tubular cavity 40 is also accessible from within the syringe barrel 16. The tubular cavity 40 creates a central post 44 within the needle base 26, wherein the central post 44 is concentric with the central axis 28. The needle 24 extends through the central post 44, therein enabling the needle 24 to access the contents of the syringe barrel 16. The central post 44 has a length, which is longer than the length of the tubular cavity 40. As a result, the central post 44 partially extends into the syringe barrel 16.

An annular spacer 46 and an activation ring 48 are provided. In the shown embodiment, the annular spacer 46 and the activation ring 48 are shown as separate components. This is an optional configuration. The annular spacer 46 and the activation ring 48 can be molded as a single piece. In the shown two-piece construction, the annular spacer 46 is tubular in shape, with inner and outer diameters that enables the annular spacer 46 to fit within the tubular cavity 40 of the needle base 26. The activation ring 48 has an annular body 49 and two radial supports 50 that extend outwardly from the annular body 49. The annular body 49 has the same inner diameter and outer diameter as the annular spacer 46. The radial supports 50 are wide enough to extend into the side slots 42 of the needle base 26. The combined length of the annular spacer 46 and the activation ring 48 are exactly the same as the length of the central post 44. The annular spacer 46 and the activation ring 48 are free to slide along the length of the central post 44, as limited by the movement of the radial supports 50 in the side slots 42.

The head subassembly 12 includes a protective cover 52 that is in place over the needle base 26. The protective cover 52 has a safety sheath 54 that surrounds part of the needle 24. The protective cover 52 can reciprocally move along the exterior of the needle base 26. However, the protective cover 52 contains an inwardly extending locking protrusion 56 that can engage the locking depressions 36, 38 on the exterior of the needle base 26. When the locking protrusion 56 moves into one of the locking depressions 36, 38, the protective cover 52 becomes biased into a set position.

Figure 4:
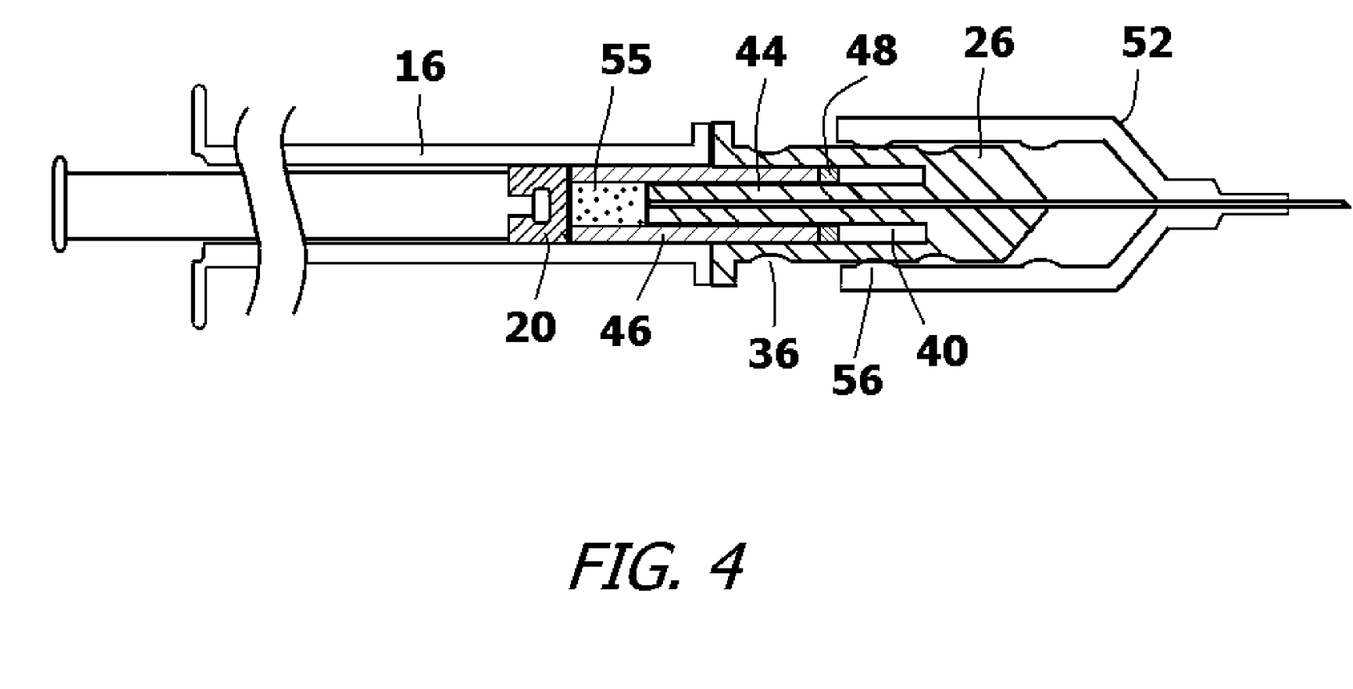
FIG. 4 is a cross-sectional view of the exemplary embodiment with the needle partially covered by the protective cover.
Figure 5:
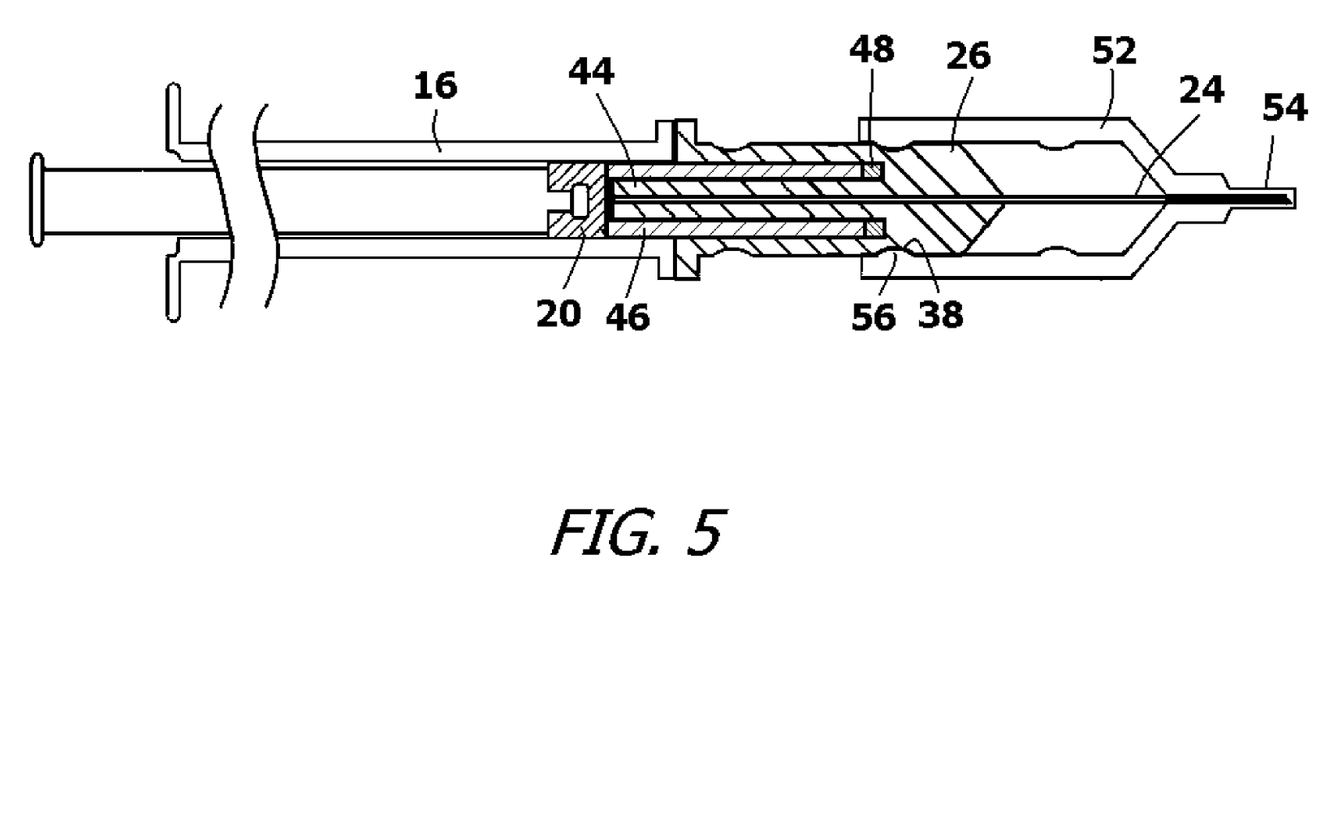
FIG. 5 is a cross-sectional view of the exemplary embodiment with the needle fully covered by the protective cover.

Prior to use, the head subassembly 12 has the configuration shown in FIG. 2. Referring to FIG. 4 and FIG. 5 in conjunction with FIG. 3, it can be seen that prior to use, the syringe barrel 16 is filled with a medication 55 in the traditional manner. In this first position, the syringe barrel 16 is full and locking protrusion 56 on the protective cover 52 engages the first locking depression 36 on the needle base 26. This prevents any inadvertent discharge from occurring while the needle and syringe system 10 is being handled. As the plunger rod 18 is manually advanced, the locking protrusion 56 can be displaced from the first locking depression 36. As the piston head 20 advances toward the head subassembly 12, the piston head 20 contacts the annular spacer 46 and presses both the annular spacer 46 and the activation ring 48 into the tubular cavity 40 around the central post 44 of the needle base 26. As the piston head 20 contacts the central post 44, the annular spacer 46 and the activation ring 48 completely fill the tubular cavity 40. All medication is displaced from the syringe subassembly 14 except for the exceedingly small volume that remains inside the needle 24. At this second position, the locking protrusion 56 engages the second locking depression 38 on the needle base 26.

As the plunger rod 18 is advanced, the plunger rod 17 contacts and moves the annular spacer 46. The annular spacer 46 moves the activation ring 48. The radial supports 50 on the activation ring 48 extend into the side slots 42 in the protective cover 52. As the activation ring 48 is pressed forward by the advancing annular spacer 46, the radial supports 50 move the protective cover 52 forward on the needle base 26. As the protective cover 52 moves forward, the safety sheath 54 also moves forward, wherein the safety sheath 54 covers the tip of the needle 24. The activation ring 48 and the radial supports 50 move along the needle 24 during the injection. As a result, the safety sheath 54 also moves forward during the injection. By the time the injection is complete, the safety sheath 54 is fully advanced and the needle 24 becomes fully shielded. As a consequence, there is no opportunity after the injection for a healthcare provider to contact the tip the needle 24.

A colored indictor may be provided on the exterior of the needle base 26 to provide a color-coded indication that the needle and syringe system 10 has moved from its full first position to its discharged second position.

It will be understood that the embodiment of the present invention that is illustrated and described is merely exemplary and that a person skilled in the art can make many variations to that embodiment. All such embodiments are intended to be included within the scope of the present invention as defined by the appended claims.

What is claimed is:

1. A needle and syringe system, comprising:
   a syringe barrel;
   a plunger rod having a plunger head that can reciprocally move within said syringe barrel;
   a needle base affixed to said syringe barrel, said needle base having a central post that extends into said syringe barrel, wherein said central post has a first length and terminates in said syringe barrel at a first end, and wherein a tubular cavity is formed in said needle base that surrounds at least part of said central post;
   slots formed in said needle base that provide lateral access into said tubular cavity;
   a needle that extends through said central post of said needle base, wherein said needle terminates at said first end of said central post;
   an annular spacer that fits within said tubular cavity;
   a ring that fits within said tubular cavity that is moved by said annular spacer, wherein said annular spacer and said ring have a combined second length that is equal to said first length of said central post;
   supports that extend from said ring and extend through said slots from within said tubular cavity;
   a protective cover that surrounds said needle base and contacts said supports;
   wherein when said plunger rod is advanced in said syringe barrel, said plunger head advances said supports in said cavity and said supports move said protective cover from a first position to a second position.

2. The system according to claim 1, wherein said needle is protected by said protective cover when said protective cover is in said second position.

3. The system according to claim 1, wherein said plunger head moves said annular spacer in said syringe barrel and said annular spacer moves said ring.

4. The system according to claim 1, wherein said needle base and said protective cover have a protrusion and depressions that engage and act to retain said protective cover in said first position and said second position.

5. A needle and syringe system, comprising:
   a syringe barrel;
   a plunger rod having a plunger head that can reciprocally move within said syringe barrel;
   a needle base affixed to said syringe barrel, said needle base having a central axis, wherein a cavity is formed in said needle base and a post extends through said cavity, wherein said cavity and said post are concentric with said central axis, and wherein said post has a first length and terminates within said syringe barrel at a first end;
   a needle that extends into said needle base along said central axis, wherein said needle extends through said post to said first end of said post and is open at said first end of said post;
   a spacer that is displaced into said cavity within said needle base as said plunger head is advanced in said syringe barrel;
   an activation ring that is moved by said spacer, wherein said spacer and said activation ring have a combined second length that is equal to said first length of said post; and
   a protective cover disposed about said needle base, wherein said activation ring moves said protective cover between a first position and a second position as said spacer is displaced into said cavity.

6. The system according to claim 5, wherein slots are formed in said needle base that provide access to said cavity.

7. The system according to claim 6, further including supports that extend from said activation ring that extend through said slots from within said cavity.

8. The system according to claim 7, wherein said protective cover contacts said supports and is moved between said first position and said second position by said supports.

9. The system according to claim 5, wherein said plunger head moves said spacer and said spacer moves said activation ring.

10. The system according to claim 5, wherein said needle base and said protective cover have a protrusion and depressions that engage and act to retain said protective cover in said first position and said second position.

11. A needle and syringe system, comprising:
    a syringe barrel;
    a plunger rod having a plunger head that can reciprocally move within said syringe barrel;
    a slotted needle base affixed to said syringe barrel, said slotted needle base having slots, a first end that faces said syringe barrel and a distal second end that faces away from said syringe barrel, wherein a tubular cavity is formed in said needle base that surrounds a central post, wherein said central post has a first length and said tubular cavity is accessible from within said syringe barrel;
    at least one spacer having a second length equal to said first length of said central post;
    supports, moved by said at least one spacer, that extend through said slots from within said cavity;
    a protective cover that surrounds said needle base, wherein said protective cover is moved by movement of said supports in said slots;
    wherein when said plunger rod is advanced in said syringe barrel, said plunger head advances said supports into said cavity and said supports move said protective cover from a first position to a second position.

12. The system according to claim 11, wherein a needle extends from said second end of said needle base and said needle is protected by said protective cover when said protective cover is in said second position.

13. The system according to claim 11, wherein said at least one spacer includes a tubular spacer and a ring, wherein said supports extend from said ring.

14. The system according to claim 13, wherein said plunger head moves said tubular spacer and said tubular spacer moves said ring.

* * * * *